(12) United States Patent
Prince et al.

(10) Patent No.: US 10,168,304 B2
(45) Date of Patent: Jan. 1, 2019

(54) RAIL INSPECTION APPARATUS AND METHOD

(71) Applicant: Sperry Rail Holdings, Inc., Shelton, CT (US)

(72) Inventors: Steven J. Prince, Norwalk, CT (US); Ján Kocur, Shelton, CT (US)

(73) Assignee: Sperry Rail Holdings, Inc., Shelton, CT (US)

( * ) Notice: Subject to any disclaimer, the term of this patent is extended or adjusted under 35 U.S.C. 154(b) by 168 days.

(21) Appl. No.: 14/996,410

(22) Filed: Jan. 15, 2016

(65) Prior Publication Data
US 2017/0205379 A1 Jul. 20, 2017

(51) Int. Cl.
*G01N 29/265* (2006.01)
*G01N 29/22* (2006.01)

(52) U.S. Cl.
CPC ......... *G01N 29/265* (2013.01); *G01N 29/225* (2013.01); *G01N 2291/2623* (2013.01)

(58) Field of Classification Search
CPC ............... G01N 29/265; G01N 29/225; G01N 2291/2623; G01N 2291/262; G01N 2291/26

USPC ........................... 73/636, 597, 598, 632, 634
See application file for complete search history.

(56) References Cited

U.S. PATENT DOCUMENTS

| | | | | |
|---|---|---|---|---|
| 5,339,692 A * | 8/1994 | Shoenhair | ............ | G01N 29/223 73/636 |
| 5,386,727 A * | 2/1995 | Searle | ................ | G01N 29/2493 73/602 |
| 2014/0142868 A1 * | 5/2014 | Bidaud | .............. | G01N 21/8803 702/40 |

* cited by examiner

*Primary Examiner* — Manish S Shah
*Assistant Examiner* — Rose M Miller
(74) *Attorney, Agent, or Firm* — McCormick, Paulding & Huber LLP

(57) ABSTRACT

An apparatus and method for rail inspection include a inspection carriage that moves atop a rail and carries a rail height sensor directed toward the rail. The rail height sensor generates a signal correlated with a vertical position (height) of the rail relative to the carriage as the carriage moves along the rail. A signal processor converts the rail height signal to a log of rail heights along the rail. Further processing of the log, e.g., in the signal processor, identifies crushed head defects in the rail.

23 Claims, 14 Drawing Sheets

RAIL INSPECTION APPARATUS AND METHOD

TECHNICAL FIELD

The invention relates, in general, to apparatus and methods for non-destructive inspection of railroad tracks to detect flaws or defects. More particularly, the invention relates to a mobile and durable inspection apparatus and methods for its use to detect and differentiate among different types of gross (large scale) rail line defects or damage.

BACKGROUND

It is well recognized in the railway industry that, either through manufacturing processes or through natural environmental processes and normal use, rails of a railroad track develop certain detrimental flaws. The flaws may include both non-critical and critical defects, for example, transverse defects, vertical shear or split head defects, horizontal shear or split head defects, rail end batter, or crushed head defects.

Safe operation on a rail may continue as long as the flaws remain noncritical. However, in time, even non-critical flaws may abscess or degrade into critical defects, and new flaws will arise. If the flaws are left unattended, the resulting defects could lead to a range of problems including catastrophic failure and train derailment. Catastrophic or even lesser failures present a financial, health and safety risk to the railway industry, transported goods and personnel, as well as surrounding homes and businesses. Such failures can be prevented, or at least decreased in frequency through routine inspection and maintenance. Further, routine maintenance can be made more cost-effective through selective repair, which is in turn facilitated by flaw detection.

To detect rail flaws or defects, ultrasonic testing has been employed. Vehicles and rail car-mounted inspection apparatus have been built to travel along the track and continuously perform ultrasonic inspection of the rails of the railroad track in situ. For example, carriage wheel type ultrasonic inspection apparatus, such as those of U.S. Pat. No. 7,850,748 or such as the Sperry® 1900 model inspection apparatus, are capable of detecting and measuring several types of microscale (internal) rail defects or flaws. However, other means are needed for detecting macroscale (external) defects such as crushed heads or localized surface collapses.

SUMMARY OF INVENTION

In accordance with the present invention, the height of a rail running surface (top of the rail) is measured and logged along the rail. Variations in the logged height from a running average height are used to detect relatively large defects such as crushed heads or localized surface collapses. The height of the running surface is measured by a rail height sensor that is mounted onto an inspection carriage. The variations of the measured height are logged in a signal processor operatively connected with the rail height sensor and with an encoder that tracks movement of the inspection carriage along the rail.

For example, in certain embodiments, the rail height sensor comprises a vertically movable follower wheel that is attached to the chassis of a carriage of an inspection apparatus, with a displacement transducer generating a signal based on the vertical travel of the follower wheel relative to the chassis as the carriage moves along a track. Such apparatus can search for undulations or waves that occur in cyclic patterns over distances along a rail. These continuous waves are of interest for maintenance operations such as grinding or re-surfacing of rails. The apparatus can map maximum and minimum rail heights along the rail in order to find and eventually grind away the high points thereby re-creating a smooth running surface.

In other embodiments, the rail height sensor may comprise a non-contact sensor in place of the follower wheel and transducer. For example, the rail height sensor may comprise a laser or other light beam or optical distance sensor; a sonic or an ultrasonic distance sensor; or a capacitive or other electrical field proximity sensor.

The apparatus can be further improved by modifications to enable differentiating among the detectable defects or flaws and in particular to enable detection of localized depressions that indicate flaws such as crushed head defects. For example, improved apparatus may use a vertical displacement transducer and a camera in combination with a rail height sensor.

For example, embodiments of the present invention provide improved carriage wheel type rail inspection apparatus that includes a microprocessor that monitors height of a rail running surface and triggers a visual image capture to help an operator in distinguishing among crushed head defects, localized surface collapses, rail end batters, undulations or corrugations, or other surface conditions based on patterns of vertical displacement. For example, the inventive apparatus looks for localized depressions of certain length and depth, which involve widening of the entire head of a rail. The apparatus makes use of running average height to establish a track reference plane, and uses a threshold deviation from the reference plane to eliminate corrugation or undulation detections. The apparatus looks for defects only within a pre-set range of wavelengths and filters longer or shorter wavelengths (undulations or corrugations). The apparatus ignores simple flatness defects by establishing an averaged height from which variations are measured and then tests the variations against depth and length criteria to extract crushed head defects. The apparatus uses a position encoder to track increments of distance traveled along a rail. At predetermined (configurable) distance increments, the apparatus samples rail height then calculates a reference plane of the rail as a running average of rail heights. The apparatus compares new height measurements to a predetermined (configurable) threshold variance from the reference plane. In case the threshold variance from the reference plane is exceeded over a predetermined (configurable) distance, then the apparatus signals a crushed head defect. The apparatus may be duplicated so as to simultaneously measure both rails of a railroad track.

Certain exemplary embodiments of the invention, as briefly described above, are illustrated by the following figures.

DETAILED DESCRIPTION

Figure 1:
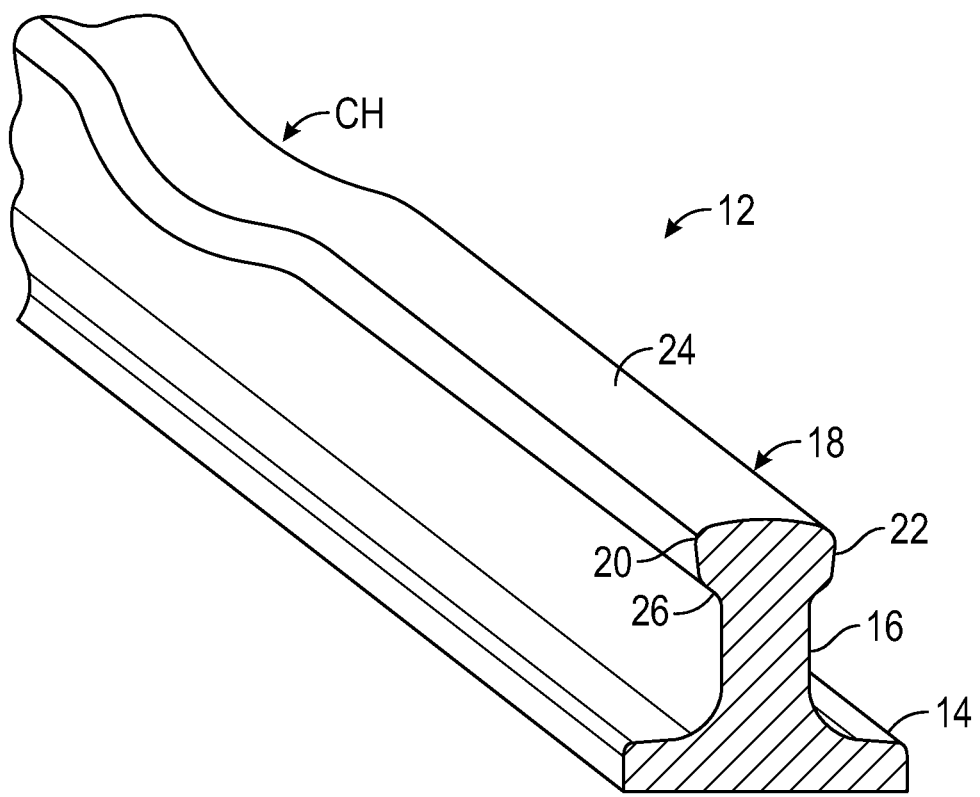
FIG. 1 shows a perspective view of a railroad rail including an exemplary crushed head defect.
Figure 2:
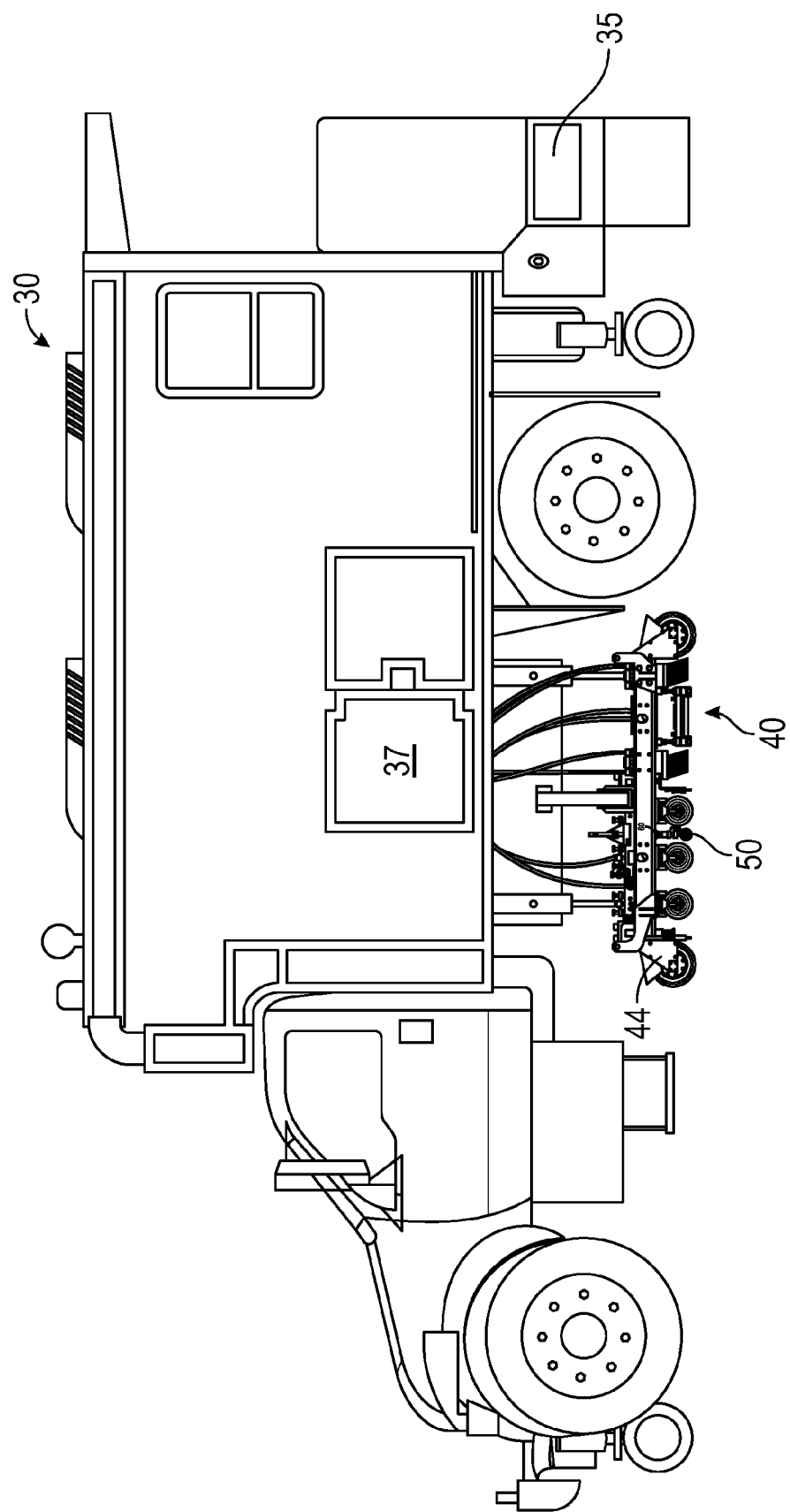
FIG. 2 shows a side view of a railroad rail inspection system or apparatus that incorporates an inspection carriage and a rail height sensor and is mounted onto a rail inspection vehicle, according to the present invention.
Figure 3:
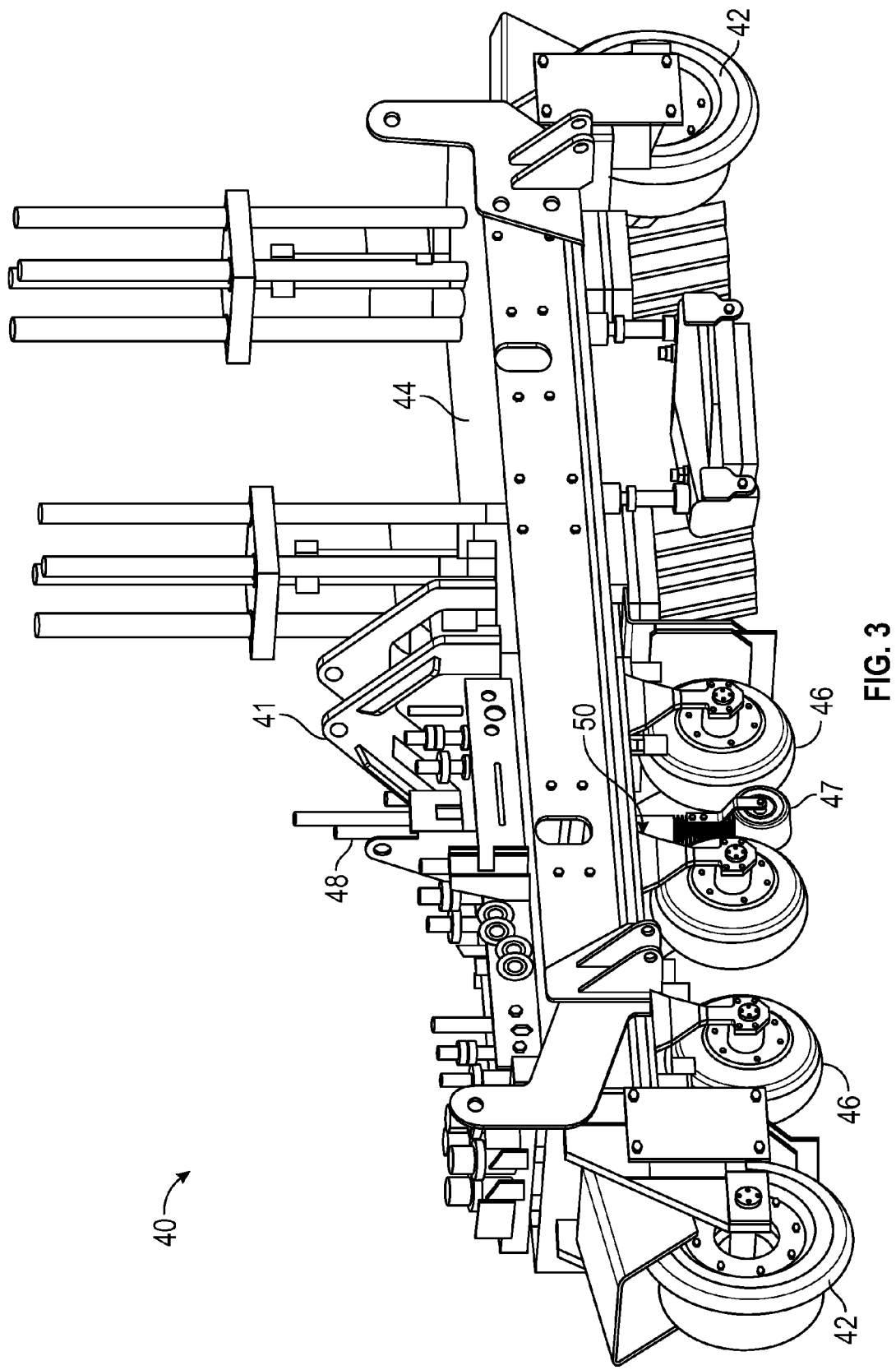
FIG. 3 shows in perspective view the inspection carriage that is mounted under the rail inspection vehicle as shown in FIG. 2.

Embodiments of the invention are shown in the drawings and are described as relating to detection of crushed head defects in rail lines. Referring to FIG. 1, a rail 12 has a typical, known rail design with a base 14, a central web 16, and head 18. The head includes a gauge side 20, a field side 22, and an upper running surface 24. A crushed head defect CH then consists of a flattened region along the rail head 18, at least several inches in length, including a crushing down of the head 18 into or beyond the head fillet 26 that joins the rail head to the underlying rail web 16. The invention relates to detecting crushed head defects, and further relates to distinguishing crushed head defects from localized surface collapse. Localized surface collapse includes flattening or widening of the rail head 18 for several inches, not extending down into the fillet 26 that joins the rail head to the underlying rail web 16, and without signs of cracking under the rail head. The invention further relates to distinguishing crushed heads and localized surface collapse from rail end batter, which is a condition resulting from mechanical impact, similar to a crushed head but arising at a joint bar that links two pieces of rail.

FIGS. 2-5 show a railroad rail inspection system or apparatus 30 and components thereof. The inspection apparatus 30 includes a camera 35, which is supported with its field of view directed laterally toward the rail 12. This camera 35 is useful for capturing sidelong images of the web 16 and of the rail head 18, which can aid an operator to distinguish true defects from false indications of defects. For example, as further discussed below, the camera 35 may be triggered to capture an image in response to detecting a rail head defect. The inspection apparatus 30 also includes an inspection carriage 40, which in an inspection operation is suspended by links 41 (FIG. 3) beneath a railcar or inspection vehicle, which travels along the rails for in situ rail flaw detection and identification. The inspection carriage 40 includes front and rear support wheels 42, mounted at longitudinal ends of the carriage chassis 44, to guide the carriage along a rail in a substantially centered position when the carriage is lowered onto the rail in an inspection operation.

The apparatus 30 also includes a horizontal position encoder 37, which is operatively connected with the carriage wheels 42 for measuring movement of the inspection carriage 40 along the rail 12, for example in 1/96" increments. The horizontal position encoder 37 generates a distance increment signal (e.g., an electrical signal of 0-5 V or 4-20 mA) for each increment of travel of the inspection carriage 40 along the rail 12.

The inspection carriage 40 may be equipped with a number of known railroad rail inspection devices and inspection accessories that operate independently or in conjunction with the present invention. For instance, the carriage may carry one or more known ultrasonic scanning wheels 46, such as shown for example in U.S. Pat. No. 7,849,748, which utilize transducers set at various angles to detect flaws ahead of and behind the wheels relative to the direction of travel, as well as defects below the carriage in the web of the rails.

Further details of the ultrasonic rail scanning wheels are not germane to the purpose and operation of the present invention for detection of gross (macroscopic) external flaws and more particularly for differentiation among several types of gross flaws such as crushed head, rail end batter, or localized surface collapse.

Accordingly, for the purpose of gross flaw detection the exemplary system 30 includes a rail height sensor 50 that is mounted on the inspection carriage 40. The rail height sensor 50 tracks a vertical distance from the inspection carriage chassis 44 to the top of the rail 12, i.e. the running surface 24 of the rail head 18. Based on this vertical distance, the rail height sensor 50 produces a signal from which a rail height is determined relative to a track reference plane, which has been established based on a moving average of the rail heights.

In the illustrated embodiments, the rail height sensor 50 comprises at least one follower wheel 47 as well as a vertical displacement transducer 48, which is mounted onto the chassis 44 proximate the follower wheel 47 so that the system 30 may monitor vertical displacement of the follower wheel 47 relative to the chassis 44. In operation, the follower wheel 47 rides along the running surface 24 of the rail 12 to track the rail height. However, in place of the follower wheel 47 and its associated transducer 48 and mounting gear as illustrated, the rail height sensor 50 can comprise of other sensor technologies. For example, the rail height sensor 50 may include a non-contact distance sensor (e.g., a laser or other light beam or optical distance sensor; a sonic or an ultrasonic distance sensor; or a capacitive or other electrical field proximity sensor) that is fixedly supported from the inspection carriage chassis 44 and that is directed from the inspection carriage chassis toward the rail running surface 24. In such case, the non-contact sensor still would produce a signal from which a rail height is determined, just as for the follower wheel 47 as further described below.

Figure 4:
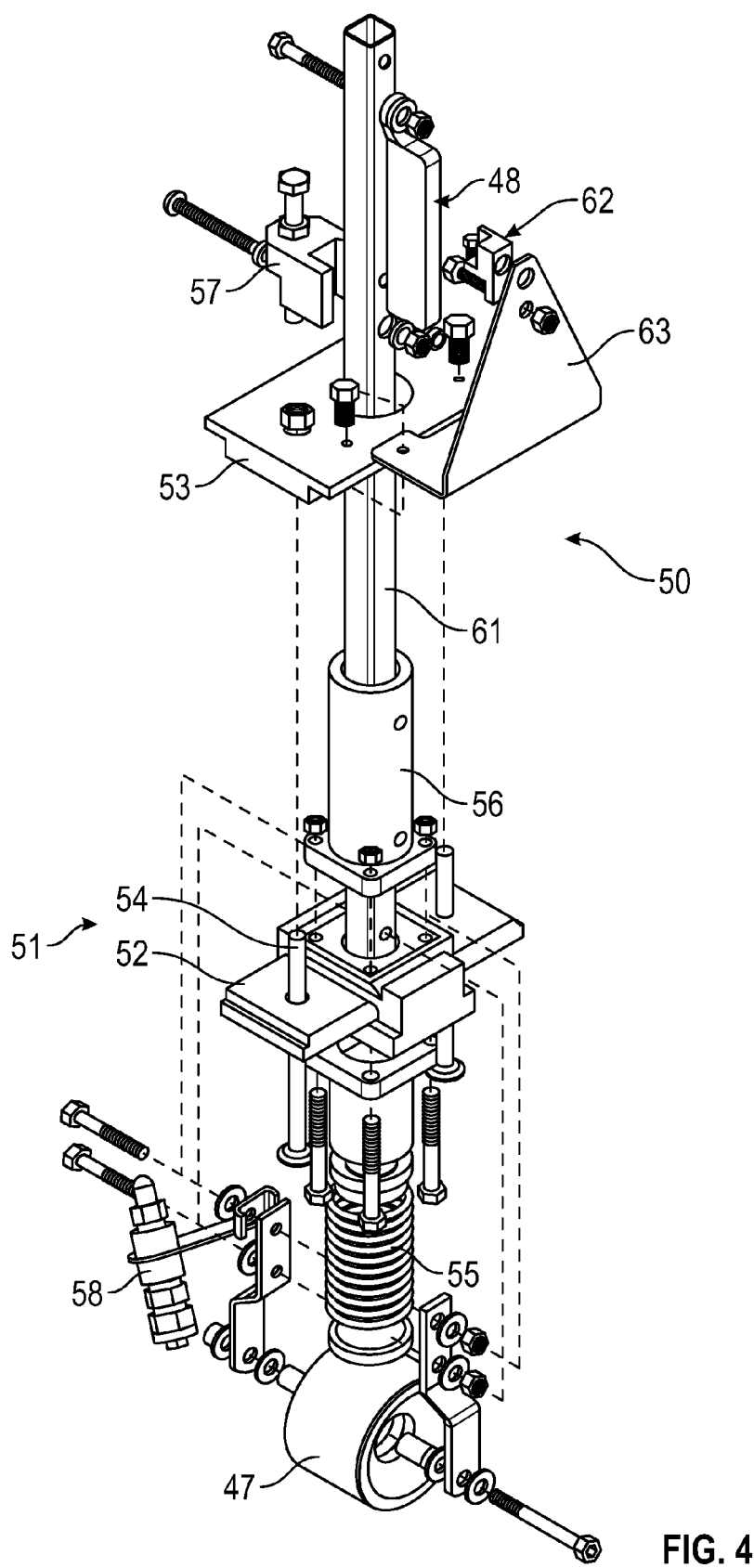
FIG. 4 shows details of a rail height sensor that is supported on the inspection carriage of FIG. 3.

The rail height sensor 50 and its mounting gear are also shown in greater detail in FIG. 4. The rail height sensor 50 may be clamped onto the chassis 44 by way of a clamp 51. The clamp 51 includes two wedges 52 as well as an upper T-plate 53. Bolts 54 draw the wedges 52 toward the T-plate 53, so that the wedges and the T-plate grip the chassis 44. This arrangement enables the rail height sensor 50 to be retrofitted into an existing inspection carriage, e.g., a carriage as shown in U.S. Pat. No. 7,849,748.

Referring still to FIG. 4, the mounting of the exemplary rail height sensor 50 onto the chassis 44 also may include a spring 55 that is arranged to press the follower wheel 47 downward against the rail running surface 24; and/or a damping sleeve 56 that supports the follower wheel from the carriage 40. Moreover, the mounting may include a mechanical stop 57 for limiting downward travel of the follower wheel 47 from the chassis 40. These components are not required in a rail height sensor 50 that comprises a non-contact sensor, which is rigidly mounted to the carriage 40. In certain embodiments, in which the rail height sensor 50 is supported from the carriage 40 between the ultrasonic scanning wheels 46, the mounting also may include an ultrasonic couplant spray nozzle 58 that is supported together with the rail height sensor 50 and is oriented toward one of the ultrasonic scanning wheels. This spray nozzle 58 permits locating the rail height sensor 50 in a position where ultrasonic couplant needs to be applied to the rail running surface 24 ahead of a scanning wheel 46.

Figure 5:
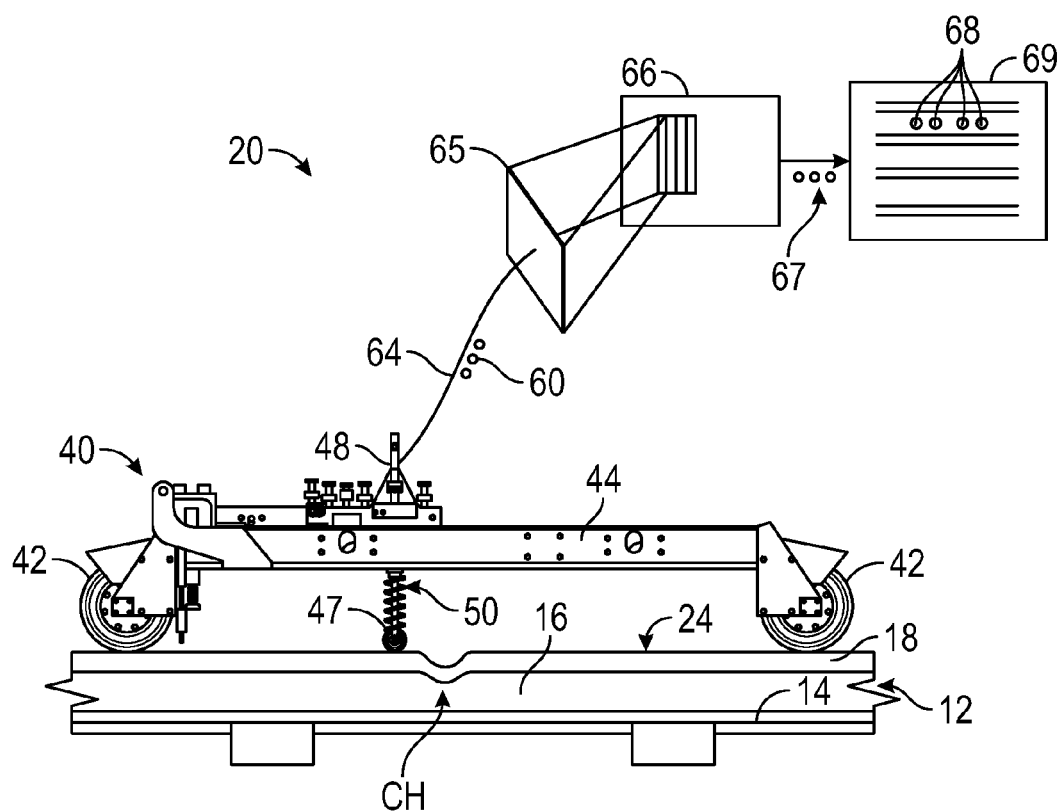
FIG. 5 shows a schematic view of the rail inspection apparatus of FIG. 2.

Referring also to FIG. 5, the rail height sensor 50 produces a vertical position signal 60 (e.g., an electrical signal of 0-5 V; 4-20 mA) that correlates to the vertical position of the follower wheel 47. For example, the transducer 48, as shown in FIG. 4, may be a linear electromagnetic transducer that is mounted onto a follower wheel shaft 61 in registry with a magnetic target 62 that is fixed onto a bracket 63. As another example, the transducer 48 may be an optical encoder that is mounted onto the bracket 63 and directed toward a sequence of markings on the follower wheel shaft 61.

As shown in FIG. 5, the vertical displacement transducer 48 (or other signal-generating component of a rail height sensor 50) can be connected by cable 64, or wirelessly, for transmitting the vertical position signal 60 to a signal processor 65 (e.g., a digital signal processor) within an existing test system 66 (e.g., a Sperry® 1900™ test system). The horizontal position encoder 37 also transmits the distance increment signals to the signal processor 65. In accordance with a method/algorithm further described below, the signal processor 65 is triggered by the distance increment signals to repetitively sample the vertical position signal 60, convert the signal 60 into digital values of rail height, and generate a digital log 67 of rail heights along the rail. With reference to the digital log 67, the signal processor 65 then identifies crushed head defects to an operator by producing indications 68 at an output 69 (e.g., a display screen or a data file) of the existing test system 66. The signal processor 65 can be adapted to accept most industrial standard displacement sensors, both contact and non-contact. In case a non-contact sensor is used, such sensor may produce a standard electrical output signal (e.g., 0-5 V; 4-20 mA) or the signal processor 65 may be adapted to accept the different signal range of any particular non-contact sensor.

In connection with identifying crushed heads based on the digital log 67, the signal processor 65 also can trigger the camera 35 for image capture in response to identifying a crushed head.

Although the vertical displacement transducer 48 is shown as operatively connected with the discrete signal processor 65, other signal processing means equally may be utilized in other embodiments of the invention. For example, signal processing can be implemented by software or firmware in a general purpose processor, a field-programmable gate array, an application specific integrated circuit, or the like.

Thus, the rail inspection apparatus 30 includes the carriage 40 having the chassis 44 extending longitudinally along the rail 12 with the front and rear wheels 42 attached to the chassis for supporting the chassis atop the rail; and the rail height sensor 50 that is supported from the chassis for following the top of the rail (measuring vertical distance from the chassis to the top of the rail). The apparatus 30 also includes the horizontal position encoder 37, which generates the distance increment signal. Certain embodiments include the transducer 48 that is attached to the chassis 44 proximate the follower wheel 47 for generating the vertical position signal 60 correlated to vertical displacement of the follower wheel with reference to the chassis. Alternatively, in certain embodiments of the apparatus a non-contact distance sensor may generate its own electrical signal corresponding to rail height, without an intermediate transducer. The apparatus 30 also includes the signal processor 65 that is operatively connected with the horizontal position encoder 37 and with the transducer 48, or with the rail height sensor 50 generally. The signal processor 65 generates the digital log 67 of rail heights, based on the vertical position signal and on the distance increment signal, and processes the digital log to identify crushed head defects and to display the defects on the console 69 or to record them in a database.

Figure 6:
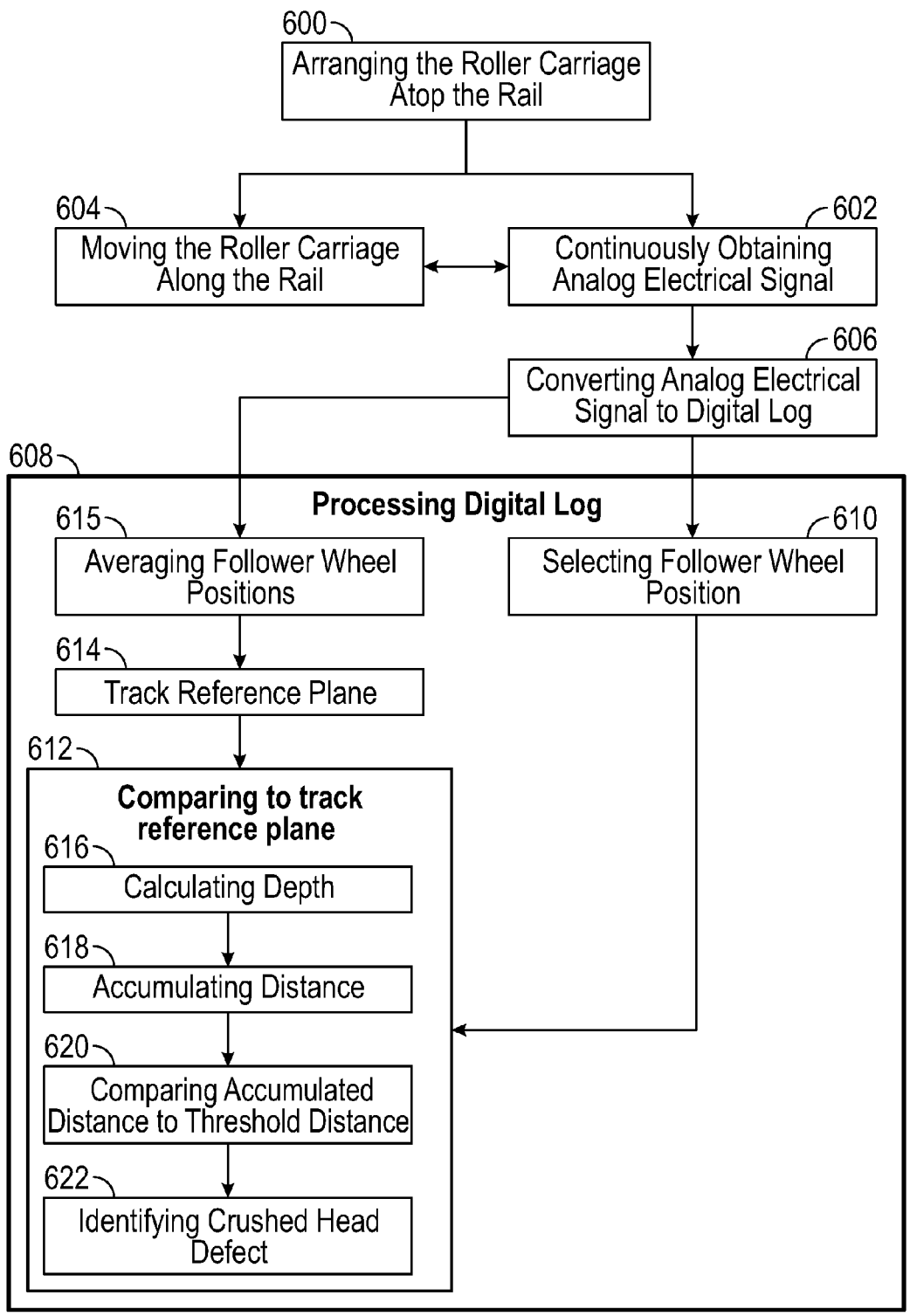
FIG. 6 shows a flowchart of a method implemented by the apparatus of FIG. 2.

Referring to FIG. 6, processing the digital log 67, within the signal processor 65, can include iteratively selecting 610 a rail height and comparing 612 the selected rail height to a track reference plane 614 established by averaging 615 rail heights that may or may not include the selected rail height. The rail height may be selected in real-time in response to the distance increment signal, or may be selected in post-processing as a position of interest. Accordingly, the digital signal processor may distinguish among crushed head, localized surface collapse, or rail end batter indications as previously defined above. Generally, crushed head defects will be sufficiently deep to deform the head weld fillet. Localized surface collapses will not be as deep as crushed heads and will extend at least several inches along the rail. Rail end batter will occur only at the end of a rail (adjacent a joint) and may be similar to either a localized surface collapse, or a crushed head. However, rail end batter typically will have a deeper and narrower downward spike of rail height.

Figure 7:
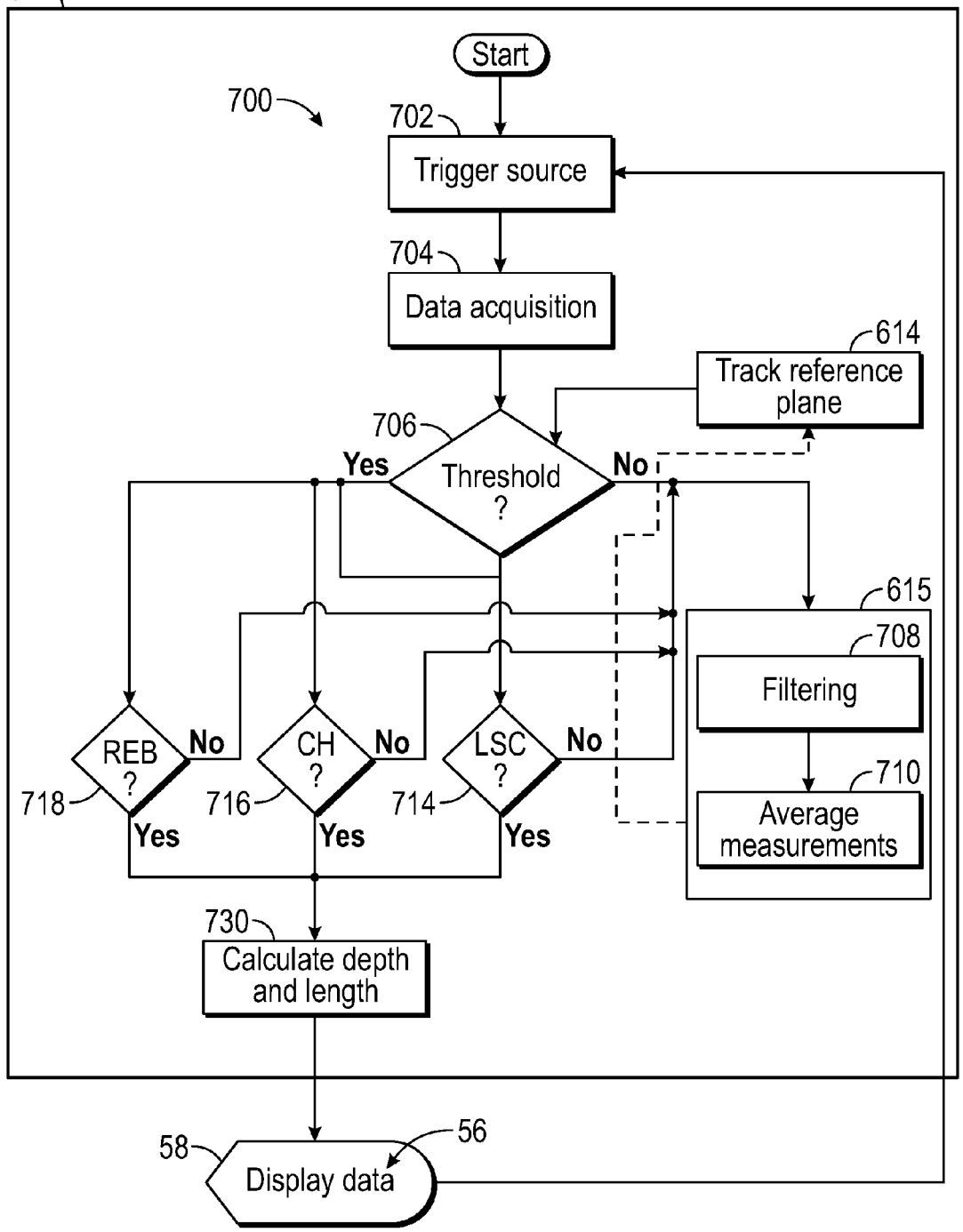
FIGS. 7-9 show flowcharts of further detail of the method of FIG. 6.
Figure 8:
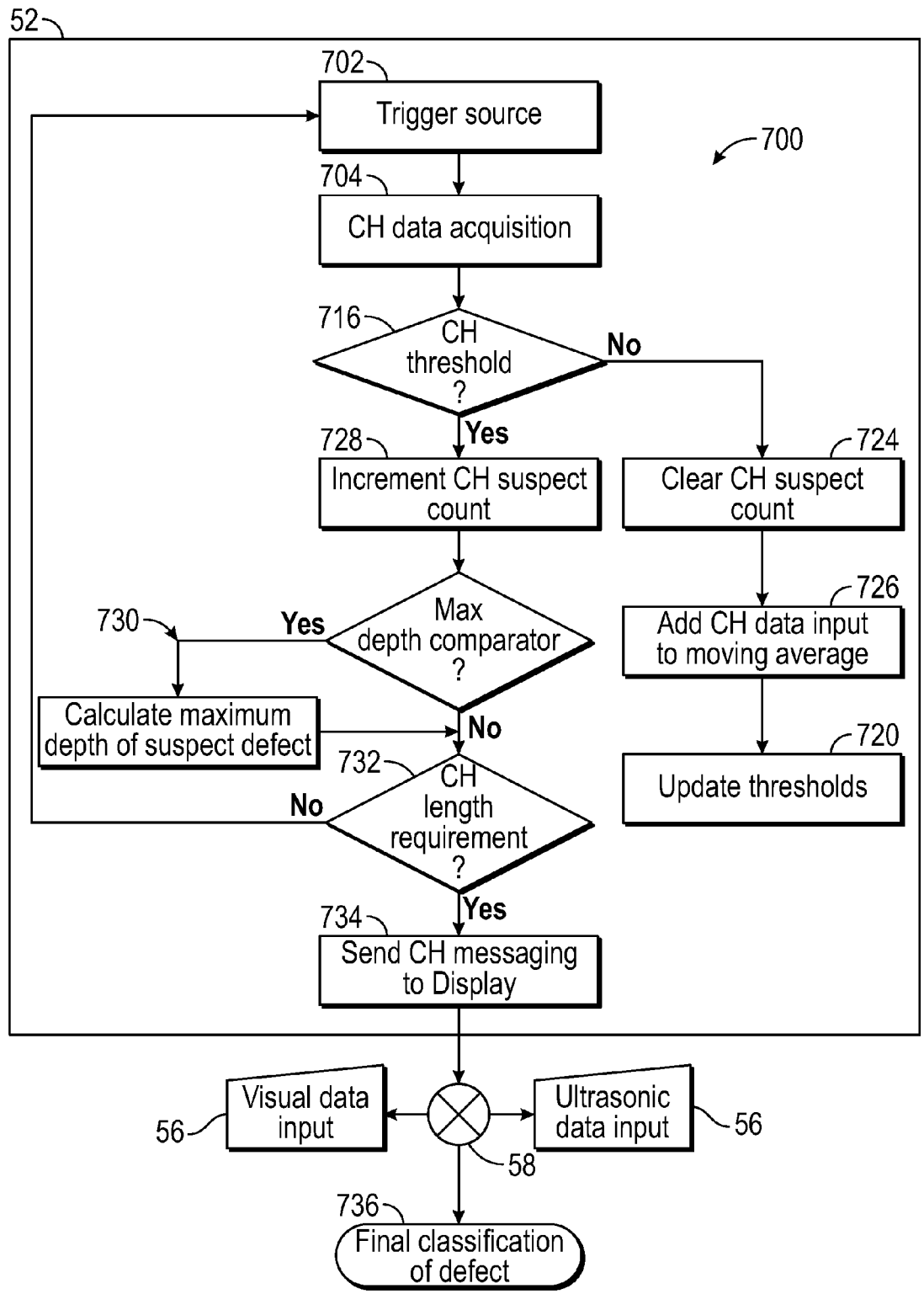
Figure 9:
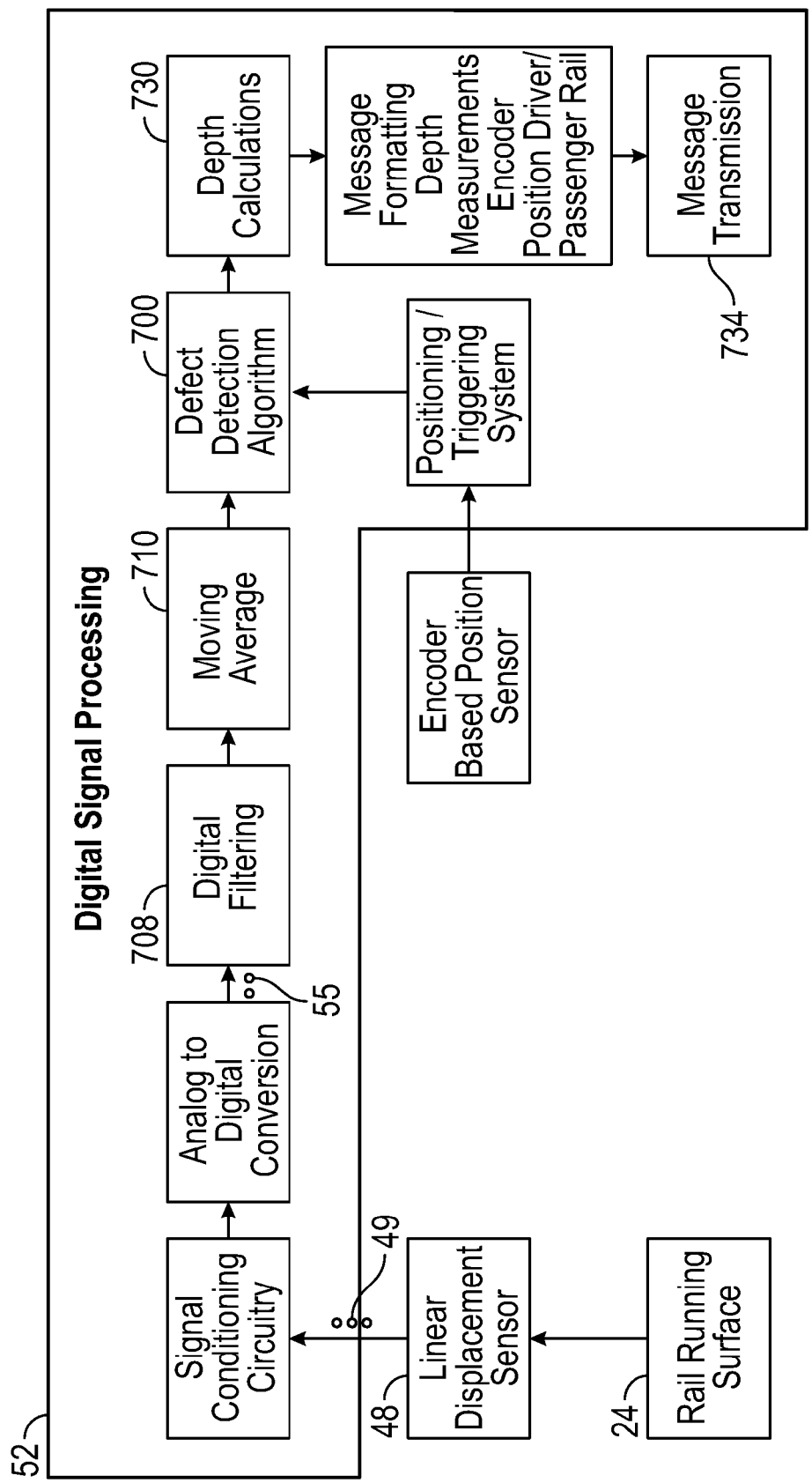

Thus, referring to FIGS. 7-9, the signal processor 65 implements a processing loop 700. At initiation of the loop 700, the signal processor 65 receives a trigger source signal 702, which can be the distance increment signal. For example, each increment of a position encoder can act as a trigger source signal. Alternatively, a trigger source can be a step change in rail height as measured by the rail height sensor 50, e.g., a step change in the vertical position of the follower wheel 47 as measured by the displacement transducer 48. The signal processor 65 acquires 704 data including the amount of change in rail height (e.g., extent of vertical displacement of the follower wheel 47) and also including the location of the inspection carriage 40 along the rail 12 as measured in 1/96" increments. The signal processor 65 then compares 706 the acquired data to a threshold value (e.g., a crushed head threshold depth below the track reference plane 614). Similar comparisons are made for threshold depths of rail end batter or localized surface collapse.

In case the threshold depth value is not exceeded, then the signal processor 65 recalculates 615 the track reference plane 614 by first filtering 708 the acquired data to eliminate changes less than a configurable noise level; then averaging 710 the filtered data to obtain the track reference plane 614.

Figure 10:
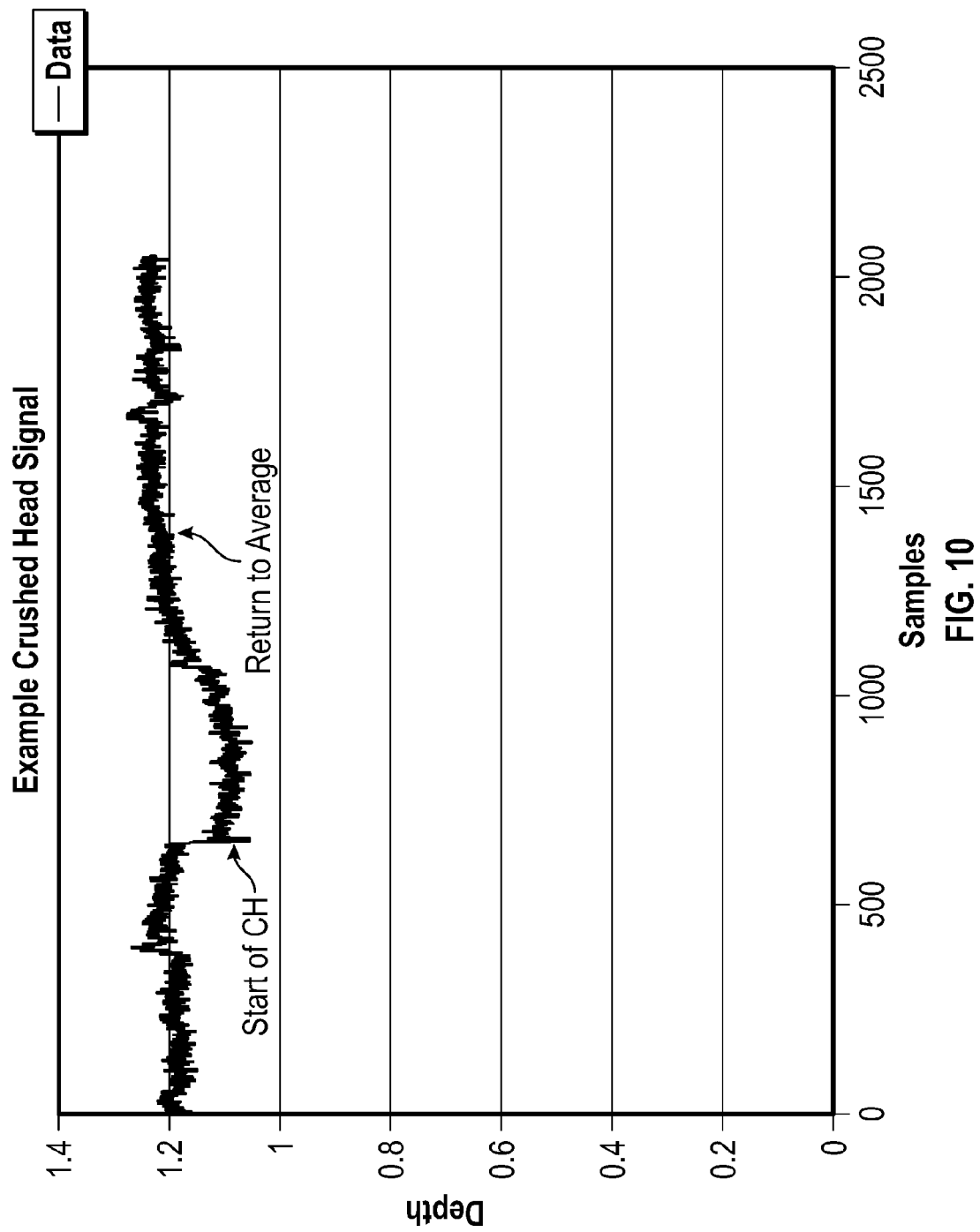
FIG. 10 shows an exemplary analog signal for localized surface collapse or crushed head.
Figure 11:
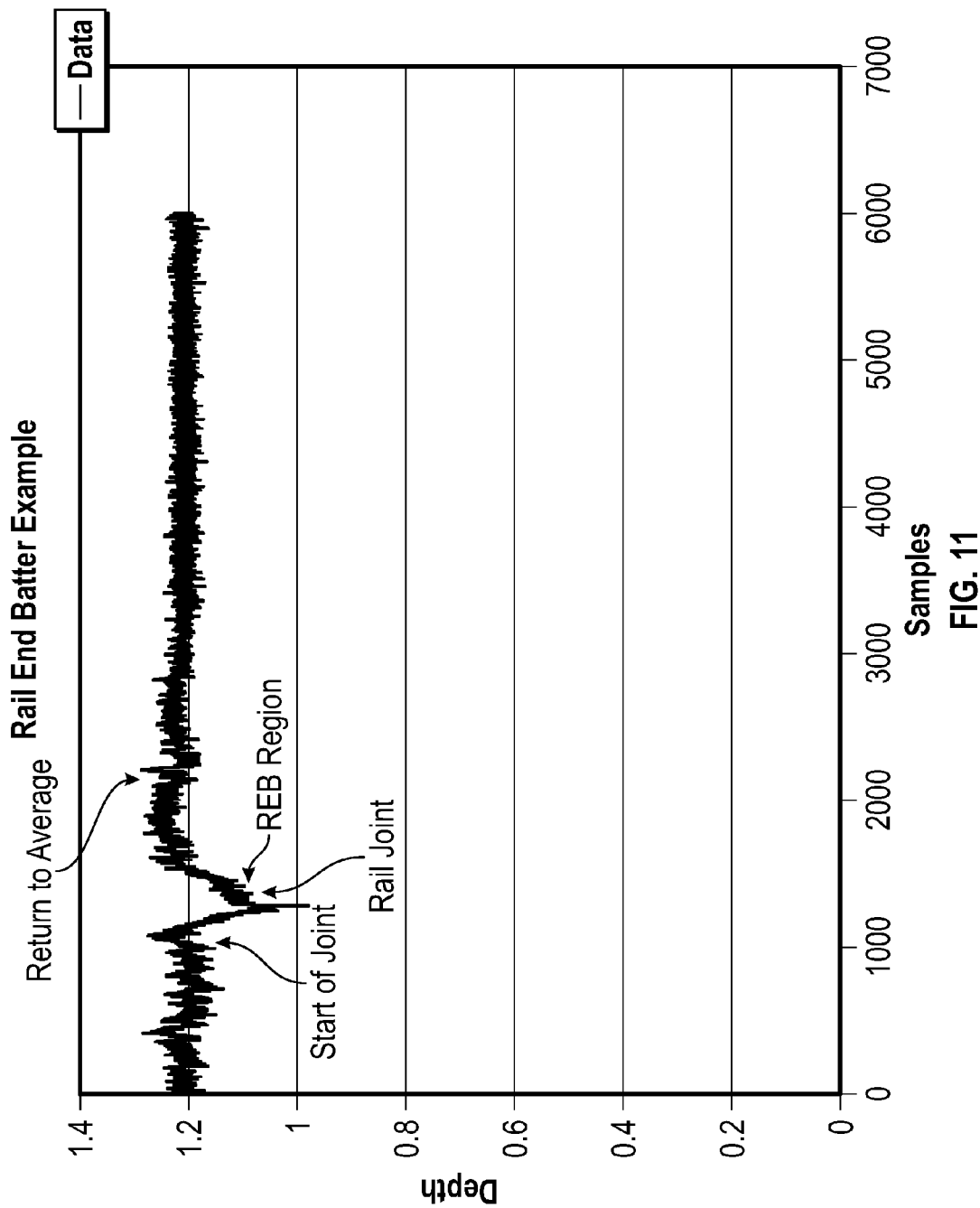
FIG. 11 shows an exemplary analog signal for rail end batter.

In case the change of rail height (e.g., vertical displacement of the follower wheel 47) exceeds the threshold depth value, then the signal processor 65 implements in parallel three screening algorithms: a localized surface collapse screen 714, a crushed head screen 716, and a rail end batter screen 718. At the localized surface collapse screen 714, the signal processor 65 checks whether the rail height (e.g., follower wheel 47 vertical position) has exceeded a first pre-set depth below the track reference plane 614, for a distance of at least several inches. (See FIG. 10). At the crushed head screen 716, the signal processor 65 checks whether the rail height has exceeded a second pre-set depth (greater than the first pre-set depth) below the track reference plane 614, for at least 3 to 8 inches. At the rail end batter screen 718, the signal processor 65 checks for a brief downward spike in the rail height, below a third pre-set depth that is greater than the first or second pre-set depths. (See FIG. 11).

In case any of the screening algorithms identifies a rail defect, the signal processor 65 then calculates 730 length and depth of the identified defect and causes display of a defect indication 56 at the output 69. In case no screening algorithm identifies any rail defect, then the signal processor 65 updates 615 the track reference plane 614 as previously discussed.

Referring to FIG. 8, the crushed head portion of the defect screening algorithm 700 is described in greater detail. After receiving 702 a trigger and acquiring 704 data, the signal processor 65 compares 716 the acquired data to the crushed head threshold value of vertical displacement. In case the acquired data does not exceed the crushed head threshold then the signal processor 65 clears 724 its crushed head suspect count and adds 726 the acquired data to the moving average of rail height, in order to support updating 615 the track reference plane 614. On the other hand, in case the acquired data does exceed the crushed head threshold, then the signal processor 65 increments 728 its crushed head suspect count and also determines 730 a maximum depth of the suspect defect. In case the crushed head suspect count is sufficiently high to exceed 732 a crushed head length requirement, then the signal processor 65 will send 734 crushed head indications 68 to the output 69. An operator then can finally classify 736 the defect as being a crushed head or anything else.

Thus, referring back to FIG. 6, aspects of the invention provide a method for rail inspection, which includes arranging 600 the roller inspection carriage 40 atop the rail 12 with the follower wheel 47 or other rail height sensor 50 directed toward the top of the rail; continuously obtaining 602 from the transducer 48 or other rail height sensor 50 a signal that correlates with a vertical position or height of the rail relative to the inspection carriage; moving 604 the roller inspection carriage 40 and the follower wheel 47 or other rail height sensor 50 along the rail 12; converting 606 the signal 60 to a log of rail heights in the signal processor 65; and processing 608 the log in the signal processor to identify crushed head defects in the rail. For example, processing the digital log includes iteratively selecting 610 a rail height and comparing 612 the selected rail height to a track reference plane 614 established by averaging 615 others of the rail heights. Comparing the rail height may include calculating 616 a depth of downward displacement from the track reference plane. Thus, processing the log also may include accumulating 618 a distance over which the calculated depth continuously exceeds a threshold depth value; comparing 620 the accumulated distance to a threshold distance value, and identifying 622 a crushed head defect in case the accumulated distance exceeds the threshold distance value. Processing may be accomplished in real time, i.e. concurrent with the acquisition of the electrical signal from the transducer 48. Processing also may be accomplished in post-processing, e.g. after a delay of seconds, minutes, hours, or days following the acquisition of the electrical signal.

Thus, referring to FIG. 9, the signal processor 65 receives the vertical position signal 60, which is produced by the transducer 48 (or other rail height sensor 50) and correlates to vertical variations of height of the rail running surface 24. The signal processor 65 also receives and is responsive to the distance increment signal produced by the horizontal position encoder 37. The signal processor 65 is triggered by the distance increment signal to acquire and condition the vertical position signal, to produce the log 67, to filter 708 the log 67, to conduct a moving average 710 to generate the track reference plane 614, and to perform the defect detection loop 700, which includes depth calculations 730. In case a defect is identified, the signal processor 65 transmits 734 a message to the display 58.

In certain aspects, the signal processor 65 may trigger the camera 35 to record an image of the rail when a crushed head defect is identified. Alternatively, during post-processing of the digital log an operator may select a portion of an image previously obtained by the camera 35 and corresponding to a rail position where a crushed head defect is identified.

Figure 12A:
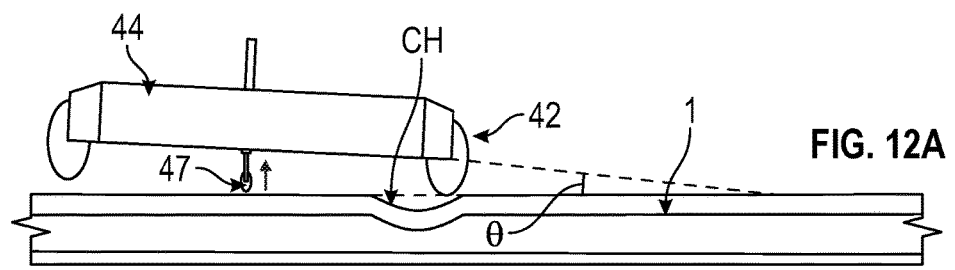
FIGS. 12A-12C show sequential schematic views of the apparatus of FIG. 2 progressing across a crushed head defect.
Figure 12B:
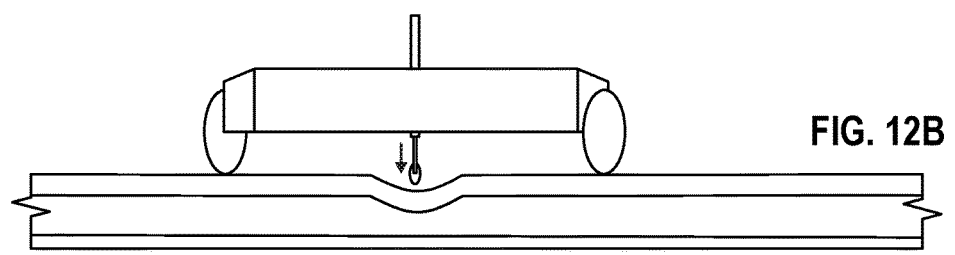
Figure 12C:
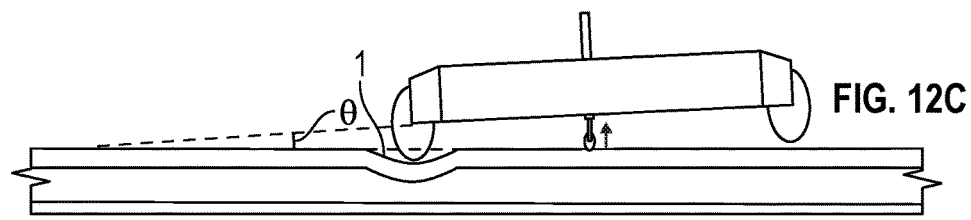

Referring to FIGS. 12A-12C, the apparatus 30 can account for an influence that the carriage support wheels 42 can have on the motion of the follower wheel 47. The signal processor 65 filters out upward motions of the follower wheel 47, caused by the carriage support wheels 42 entering a crushed head defect as shown in FIG. 12A and exiting a crushed head defect as shown in FIG. 12C, by triggering on only downward motion of the follower wheel within a crushed head defect as shown in FIG. 12B. Since the electrical signal from the transducer 48 is on an absolute scale, any increase in the signal (as caused by the interaction of the carriage support wheels 42 with the crushed head defect CH) will be automatically added to the average track reference plane and will bypass the detection algorithms.

Figure 13:
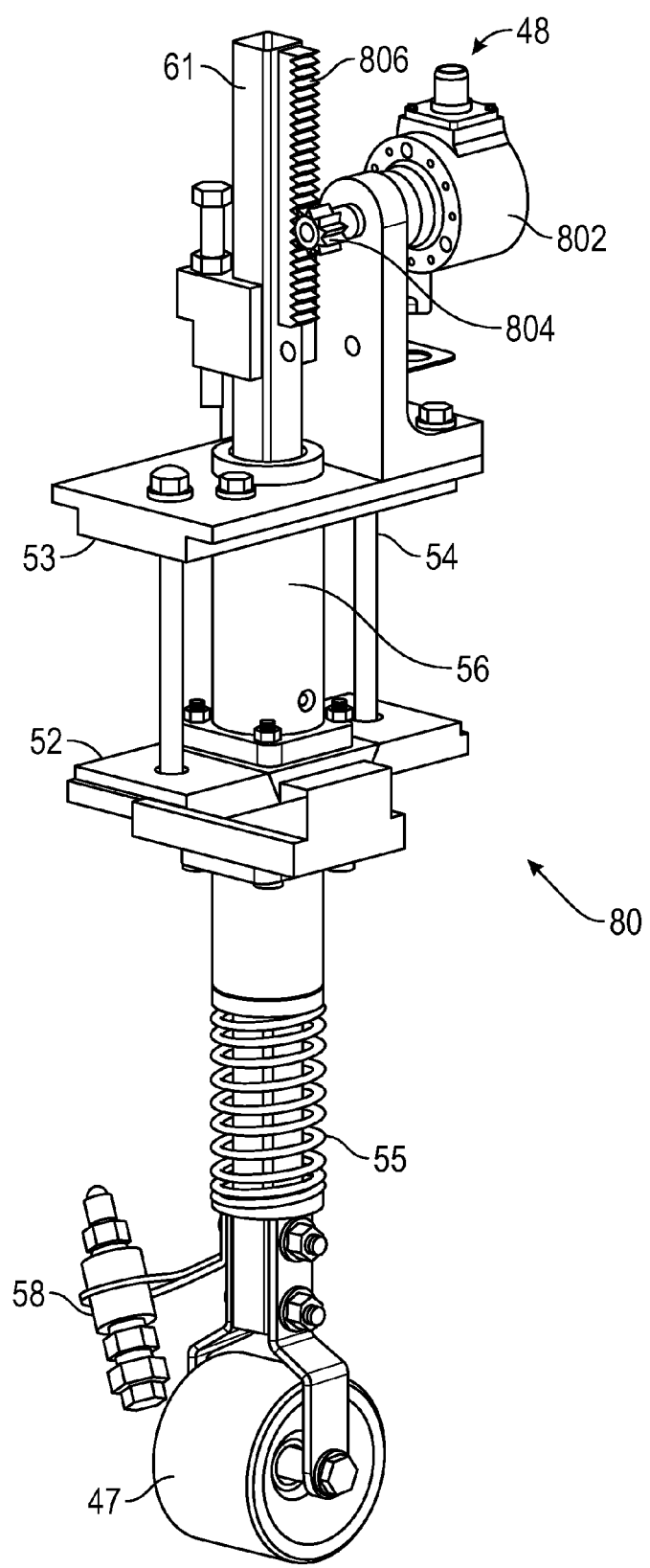
FIG. 13 shows another embodiment of the rail height sensor according to the present invention.

As mentioned, when the rail height sensor 50 comprises a follower wheel 47 it also may include a vertical displacement transducer of varying structure. For example, FIG. 13 illustrates an embodiment 80 of the rail height sensor in which a vertical displacement transducer 48 includes a rotary optical encoder 802, a pinion 804, and a rack 806 that is formed on the follower wheel shaft 61.

Figure 14:
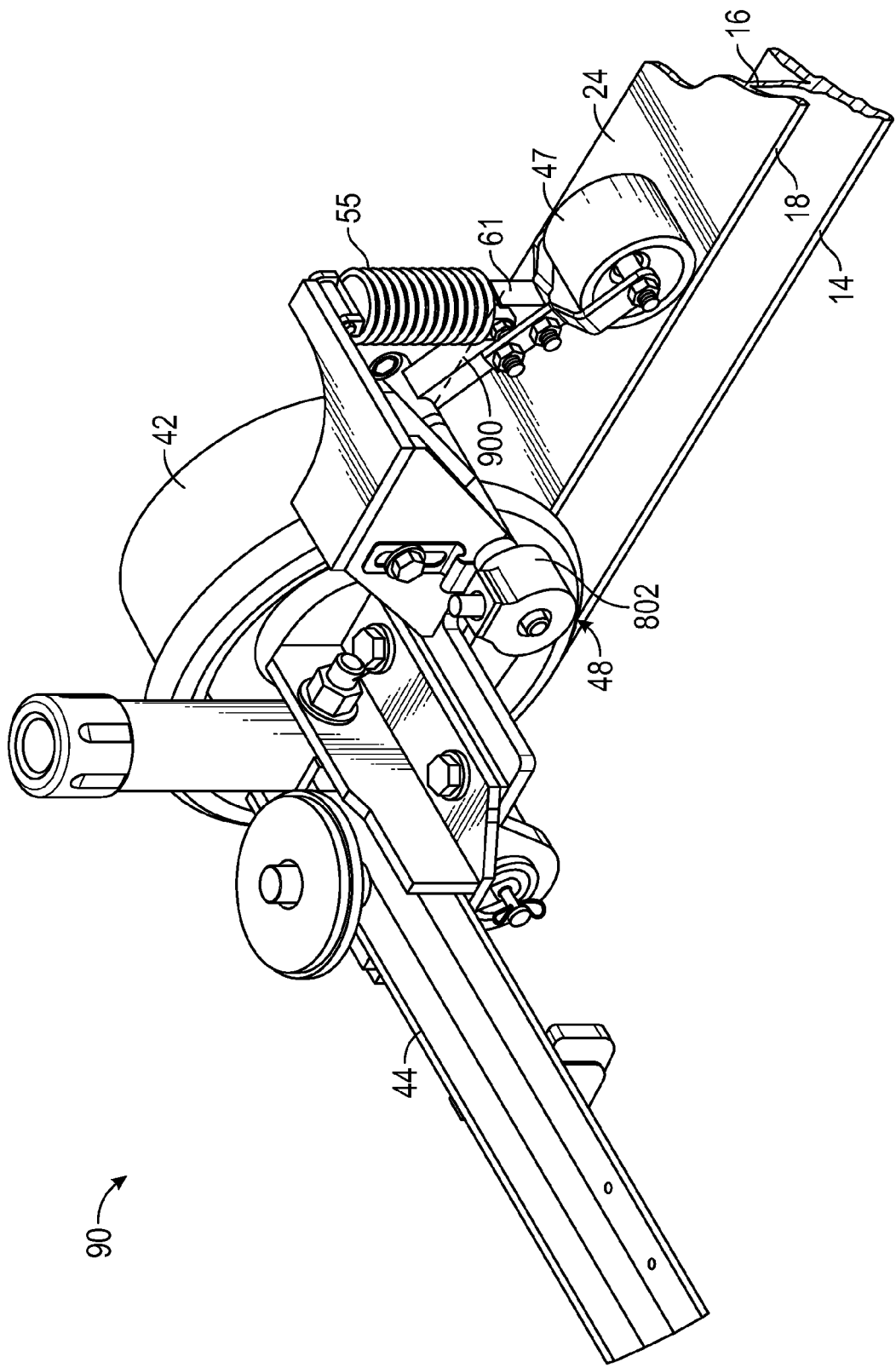
FIG. 14 shows another embodiment of the rail height sensor according to the present invention.

FIG. 14 illustrates another embodiment 90 of the rail height sensor, in which the vertical displacement transducer 48 is embodied by a rotary optical encoder 802 that is connected with the follower wheel shaft 61 by way of a swing arm 900. In such embodiments, the signal processor 65 calculates vertical linear displacement from the fractional rotation of the optical encoder, in a manner familiar to the ordinary skilled worker.

The invention may have embodiments beyond those described above with reference to inspection of traditional railways. The specification and drawings are, accordingly, to be regarded as illustrative rather than restrictive or comprehensive in nature. Although exemplary embodiments of the invention have been described with reference to attached drawings, those skilled in the art nevertheless will apprehend variations in form or detail that are consistent with the scope of the invention as defined by the appended claims. Thus, it is not intended to limit the invention other than as indicated by the appended claims.

What is claimed is:

1. A rail inspection apparatus comprising:
   a carriage having a chassis and front and rear wheels attached to the chassis to support the carriage for movement atop a rail;
   a rail height sensor supported on the chassis for establishing a point of contact moveable along the top of the rail, and producing a signal corresponding to a distance from the chassis to the top of the rail;
   a horizontal position encoder producing a signal tracking movement of the carriage along the rail; and
   a signal processor operatively connected with the rail height sensor and responsive to the horizontal position encoder for converting the rail height sensor signal to a log of rail heights along the rail, and processing the log of rail heights to identify crushed head defects and display the defects at a console and/ or record the defects in a database.

2. The apparatus of claim 1 wherein the rail height sensor comprises a follower wheel supported from the chassis for establishing the point of contact and moving along the top of the rail; and a transducer attached to the chassis proximate the follower wheel and generating a signal correlated to vertical displacement of the follower wheel with reference to the chassis.

3. The apparatus of claim 2, further comprising a spring arranged to press the follower wheel downward against the top of the rail.

4. The apparatus of claim 2, further comprising a damping sleeve supporting the follower wheel from the chassis.

5. The apparatus of claim 2, further comprising a mechanical stop for limiting downward travel of the follower wheel from the chassis.

6. The apparatus of claim 2, wherein the follower wheel is supported from the chassis in line with a plurality of ultrasonic scanning wheels attached to the carriage, further comprising an ultrasonic couplant spray nozzle supported from the carriage together with the follower wheel and oriented toward one of the plurality of ultrasonic scanning wheels.

7. The apparatus of claim 2, wherein the transducer is a linear electromagnetic transducer.

8. The apparatus of claim 2, wherein the transducer is a rotary optical encoder.

9. The apparatus of claim 8, wherein the transducer measures rotation relative to the chassis of a swing arm that connects the follower wheel to the chassis.

10. The apparatus of claim 1, further comprising a camera operatively connected with the signal processor and with its field of view directed laterally toward the rail;
wherein the signal processor triggers the camera for image capture in response to identifying a crushed head defect.

11. The apparatus of claim 1, wherein the signal processor has an algorithm that is used to distinguish between a crushed head and localized surface collapse or rail end batter indications.

12. The apparatus of claim 1, wherein the signal processor has an algorithm that is used to distinguish between a crushed head, localized surface collapse, or rail end batter based on the length over which the rail height exceeds a threshold depth below a track reference plane.

13. The apparatus of claim 12, wherein the signal processor excludes indications of defects that exceed maximum or minimum lengths.

14. A method for rail inspection comprising:
arranging an inspection carriage atop a rail with a rail height sensor mounted on the carriage and in contacting relationship with and moveable along the top of the rail;
moving the carriage and the rail height sensor along the top of the rail;
obtaining from a horizontal position encoder, at a signal processor, a signal correlated with a movement of the carriage along the rail;
obtaining from the rail height sensor, at the signal processor in response to the horizontal position encoder signal, a signal correlated with a vertical distance from the carriage to the top of the rail;
converting the vertical distance signal to a rail height in the signal processor;
storing the rail height in a log of rail heights; and
processing the log of rail heights in the signal processor to identify crushed head defects in the rail.

15. The method of claim 14, further comprising the signal processor triggering a camera to record an image of the rail when a crushed head defect is identified.

16. The method of claim 14, further comprising selecting a portion of a camera image corresponding to a rail position where a crushed head defect is identified.

17. A rail inspection apparatus comprising:
a carriage having a chassis and front and rear wheels attached to the chassis to support the carriage for movement atop a rail;
a rail height sensor supported on the chassis and producing a signal corresponding to a distance from the chassis to the top of the rail;
a horizontal position encoder producing a signal tracking movement of the carriage along the rail; and
a signal processor operatively connected with the rail height sensor and responsive to the horizontal position encoder wherein the signal processor is configured to convert the rail height sensor signal to a log of rail heights, process the log of rail heights by iteratively selecting a rail height and comparing the selected rail height to a track reference plane established by averaging other of the rail heights to identify crushed head defects for display and/ or recording.

18. The apparatus of claim 17, wherein the signal processor is triggered by the encoder to select a most recently sampled rail height and to compare the most recently sampled rail height to the track reference plane.

19. A method for rail inspection comprising:
arranging an inspection carriage atop a rail with a rail height sensor mounted on the carriage and directed toward the top of the rail;
moving the carriage and the rail height sensor along the rail;
obtaining from a horizontal position encoder, at a signal processor, a signal correlated with a movement of the carriage along the rail;
obtaining from the rail height sensor, at the signal processor in response to the horizontal position encoder signal, a signal correlated with a vertical distance from the carriage to the top of the rail;
converting the vertical distance signal to a rail height in the signal processor;
storing the rail height in a log of rail heights; and
processing the log of rail heights in the signal processor to identify crushed head defects in the rail, including iteratively selecting a rail height and comparing the selected rail height to a track reference plane established by averaging other of the rail heights.

20. The method of claim 19, wherein the step of comparing the selected rail height includes calculating a depth of downward displacement from the track reference plane.

21. The method of claim 20, wherein the step of processing the log includes tracking a distance along the rail over which the calculated depth continuously exceeds a threshold depth value.

22. The method of claim 21, wherein the step of processing the log includes comparing the tracked distance along the rail to a threshold distance value, and identifying a crushed head defect in case the tracked distance along the rail exceeds the threshold distance value.

23. The method of claim 21, further comprising excluding indications of defects that exceed maximum or minimum distances.

\* \* \* \* \*